United States Patent
Caduff et al.

(10) Patent No.: US 7,315,767 B2
(45) Date of Patent: Jan. 1, 2008

(54) IMPEDANCE SPECTROSCOPY BASED SYSTEMS AND METHODS

(75) Inventors: Andreas Caduff, Zürich (CH); Etienne Hirt, Cham (CH); Thomas W. Schrepfer, Oberbözberg (CH)

(73) Assignee: Solianis Holding AG, Zug (CH)

( * ) Notice: Subject to any disclaimer, the term of this patent is extended or adjusted under 35 U.S.C. 154(b) by 548 days.

(21) Appl. No.: 10/656,997

(22) Filed: Sep. 5, 2003

(65) Prior Publication Data

US 2004/0147819 A1 Jul. 29, 2004
US 2006/0004269 A9 Jan. 5, 2006

Related U.S. Application Data

(63) Continuation-in-part of application No. 09/980,661, filed as application No. PCT/IB01/00334 on Mar. 6, 2001.

(60) Provisional application No. 60/408,377, filed on Sep. 5, 2002.

(51) Int. Cl.
 G05B 21/00 (2006.01)
 B32B 5/02 (2006.01)
 C12Q 1/68 (2006.01)
 G01N 15/06 (2006.01)
 A61B 5/05 (2006.01)

(52) U.S. Cl. .............. 700/266; 422/50; 422/68.1; 422/82.01; 436/43; 436/63; 436/66; 436/86; 436/87; 436/95; 436/149; 600/300; 600/347; 600/365; 600/547

(58) Field of Classification Search ............. 422/50, 422/68.1, 82.01; 436/43, 63, 66, 86, 87, 436/95, 149; 700/266; 600/300, 347, 365, 600/547
See application file for complete search history.

(56) References Cited

U.S. PATENT DOCUMENTS

| | | | |
|---|---|---|---|
| 4,020,830 A | 5/1977 | Johnson et al. | 128/2 E |
| 4,180,771 A | 12/1979 | Guckel | 324/71 SN |
| 4,397,714 A | 8/1983 | Janata et al. | 204/1 T |
| 4,445,885 A * | 5/1984 | Kifune | 604/28 |
| 4,509,531 A | 4/1985 | Ward | 374/142 |
| 4,679,426 A | 7/1987 | Fuller et al. | 73/53 |
| 4,765,179 A | 8/1988 | Fuller et al. | 73/53 |
| 4,875,486 A | 10/1989 | Rapoport et al. | 128/653 |

(Continued)

FOREIGN PATENT DOCUMENTS

AT 395 075 B 9/1992

(Continued)

OTHER PUBLICATIONS

Choleau et al. *Diabetes*, 51:3263-3273 (2002).

(Continued)

*Primary Examiner*—Brian Sines
(74) *Attorney, Agent, or Firm*—Mintz, Levin, Cohn, Ferris, Glovsky and Popeo, P.C.

(57) ABSTRACT

One aspect of the invention provides a device that non-invasively determines the concentration of a substance in a target. The device includes a first electrode, a measuring circuit, and a data processor. In one embodiment of the device, the first electrode can be electrically insulated from the target, e.g., a cover layer of insulating material covers the first electrode.

17 Claims, 7 Drawing Sheets

U.S. PATENT DOCUMENTS

| | | | | |
|---|---|---|---|---|
| 4,965,206 | A | 10/1990 | Kell | 435/291 |
| 5,050,612 | A | 9/1991 | Matsumura | 128/670 |
| 5,077,476 | A | 12/1991 | Rosenthal | 250/341 |
| 5,109,855 | A | 5/1992 | Gunter | 128/653.1 |
| 5,353,802 | A | 10/1994 | Ollmar | 128/734 |
| 5,508,203 | A | 4/1996 | Fuller et al. | 436/149 |
| 5,771,891 | A | 6/1998 | Gozani | 128/635 |
| 5,792,668 | A | 8/1998 | Fuller et al. | 436/149 |
| 5,804,967 | A | 9/1998 | Miller et al. | 324/314 |
| 5,890,489 | A | 4/1999 | Elden | 128/898 |
| 6,028,433 | A | 2/2000 | Cheiky-Zelina et al. | 324/663 |
| 6,182,504 | B1 | 2/2001 | Gaisford | 73/61.43 |
| 6,309,884 | B1 | 10/2001 | Cooper et al. | 436/14 |
| 6,320,393 | B1 | 11/2001 | Yasui et al. | 324/663 |
| 6,356,776 | B1 | 3/2002 | Berner et al. | 600/347 |
| 6,517,482 | B1 | 2/2003 | Elden et al. | 600/309 |
| 6,565,509 | B1 | 5/2003 | Say et al. | 600/365 |
| 6,723,048 | B2 | 4/2004 | Fuller | 600/365 |
| 6,954,662 | B2 | 10/2005 | Freger et al. | 600/316 |
| 2002/0106709 | A1 | 8/2002 | Potts et al. | 435/14 |
| 2002/0155615 | A1 | 10/2002 | Novikov et al. | 436/149 |
| 2003/0153821 | A1 | 8/2003 | Berner et al. | 600/345 |
| 2004/0104736 | A1 | 6/2004 | Cohen et al. | 324/692 |
| 2004/0133353 | A1 | 7/2004 | Geutebrück | 702/19 |
| 2004/0147819 | A1 | 7/2004 | Caduff et al. | 600/316 |
| 2004/0240512 | A1 | 12/2004 | Pesach | 374/43 |
| 2005/0101842 | A1 | 5/2005 | Suda | 600/300 |
| 2005/0113662 | A1 | 5/2005 | Djennati et al. | 600/407 |

FOREIGN PATENT DOCUMENTS

| | | |
|---|---|---|
| DE | 30 17 168 A1 | 11/1981 |
| DE | 44 46 346 A1 | 6/1996 |
| DE | 100 35 415 A1 | 1/2002 |
| EP | 0 236 434 B1 | 9/1987 |
| EP | 0298441 | 1/1989 |
| EP | 0309085 | 3/1989 |
| EP | 1 092 386 A1 | 4/2001 |
| GB | 2 033 575 A | 5/1980 |
| GB | 2 055 206 A | 2/1981 |
| GB | 1599241 | 9/1981 |
| GB | 2 100 864 A | 1/1983 |
| RU | 2 069 863 C1 | 11/1996 |
| RU | 2073242 C1 | 2/1997 |
| RU | 2088927 C1 | 8/1997 |
| SU | 1698724 A1 | 12/1991 |
| WO | WO85/04481 | 10/1985 |
| WO | WO93/18395 | 9/1993 |
| WO | WO93/18402 | 9/1993 |
| WO | WO95/04496 | 2/1995 |
| WO | WO97/39341 | 10/1997 |
| WO | WO98/09566 | 3/1998 |
| WO | WO98/04190 | 5/1998 |
| WO | WO98/38904 | 11/1998 |
| WO | WO99/44495 | 10/1999 |
| WO | WO99/39627 | 12/1999 |
| WO | WO 00/09996 | 2/2000 |
| WO | WO 00/43759 | 7/2000 |
| WO | WO 01/26538 | 4/2001 |
| WO | WO 01/36952 A1 | 5/2001 |
| WO | WO 01/47415 | 7/2001 |
| WO | WO 02/062214 A1 | 8/2002 |
| WO | WO 02/069791 A1 | 9/2002 |
| WO | WO 02/073179 A1 | 9/2002 |
| WO | WO 03/017834 A1 | 3/2003 |

OTHER PUBLICATIONS

Feldman et al. *Colloid Polymer Sci.,* 270:768-780 (1992).

Feldman et l. *Rev. Sci. Instrum.,* 67(9):3208-3216 (1996).

"General Linear Least Squares", *Numerical Recipes in C: the Art of Scientific Computing,* pp. 671-681, 1988-1992, http://www.nr.com.

Khalil, O., *Diabetes Technol. Therap.,* 6(5):660-695 (2004).

Patent Abstracts of Japan for JP 62-083649 (Matsushita Electric Ind. Co. Ltd.) (Apr. 17, 1987).

Patent Abstracts of Japan for JP 9-201337 (Casio Comput Co. Ltd.) (Aug. 5, 1997).

Patent Abstracts of Japan for JP 2000-162176 (Omron Corp.)(Jun. 16, 2000).

International Search report for PCT IB 01/00334, mailed Nov. 21, 2001.

Katz, Murray, A. (1973). "Hyperglycemia-Induced Hyponatremia Calculation of Expected Serum Sodium Depression" *The New England Journal of Medicine* 289(14):843-844.

Shalwitz, et al. (1991). "Effect of Hyperglycemia on Plasma Sodium and Potassium Concentration Revisited" *Clinical Chemistry* 37(2):293-294.

Smith, Geoff (2001). "Dielectric Spectroscopy" http://www.appsci.dmu.ac.uk/gsmith/Research/smith_ds1.thm (Printed on Nov. 15, 2001).

Naschansky, Kristen M. (2001). "Rapid Detection of Listeria Monocytogenes Employing Immunomagnetic Separation and Electrical Impedance Spectroscopy" *Food Saftey Engineering Project/Rapid Detection of L. monocytogenes*: http://foodsafety.agad.purdue.edu/research/gradprojects/naschansky.shtml (Printed on Nov. 15, 2001).

"FDA Panel Recommends Approval of Watch-Like Glucose Monitor" (1999). http://www.helioshealth.com/cgi-bin/news/news.cgi?59 (Printed on Apr. 25, 2002).

Selingo, Jeffrey (2001). "Giving Diabetics (and Their Sore Fingers) a Break" *The New York Times* Jul. 5, 2001 (Thursday):E5.

"Non-invasive Blood Glucose Monitoring" *Pindi Products Inc./* http://www.google.com/search?q=cache.wLfLsc5ZvcY:www.pindi.com/nibgm.html?pindi . . . - (Printed on Jun. 22, 2001).

"Glucose Detector" *Pindi Products, Inc./* http:www.google.com/search?q=cache:rls86NFXUZk:www.pindi.com/research.html=pindi . . . (Printed on Jun. 22, 2001).

Mendosa, Rick (2001). "Part 14: Blood Glucose Meters" *On-line Diabetes Resources/* http://www.mendosa.com/meters.htm (Printed Nov. 5, 2001).

* cited by examiner

IMPEDANCE SPECTROSCOPY BASED SYSTEMS AND METHODS

CROSS-REFERENCE TO RELATED APPLICATIONS

This application claims priority to, and benefit of, U.S. provisional patent application Ser. No. 60/408,377, filed Sep. 5, 2002, entitled "METHODS AND DEVICES FOR DETERMINING THE CONCENTRATION OF A SUBSTANCE IN A TARGET" and incorporated herein by reference in its entirety. This application is a continuation-in-part of U.S. patent application Ser. No. 09/980,661, filed Nov. 15, 2001 and entitled "Method and Device for Determining the Concentration of a Substance in Body Liquid" which was the national stage of International Application No. PCT/IB01/00334, filed Mar. 6, 2001 and entitled "Method and Device for Determining the Concentration of a Substance in Body Liquid."

TECHNICAL FIELD

The invention relates to systems, methods and devices for non-invasively determining the concentration of a substance in a target. Examples of targets include an in-vitro or an in-vivo target containing body liquid, a non-body liquid target such as wastewater or beer, and a non-liquid target such as baby food or biological tissue. One can apply the invention in fields such as biotechnology, medicine, industry, environmental monitoring, agriculture, and manufacturing (such as food manufacturing).

BACKGROUND OF THE INVENTION

One application of conventional impedance spectroscopy is to attempt to determine the concentration of glucose and other substances in body fluids. In particular, this technology is of substantial interest for the determination of glucose concentration in blood and/or inter— or intracellular liquid.

It is well known that glucose and electrolyte concentrations vary in blood and underlying tissues. Several techniques for providing glucose analysis are known. These techniques permit subjects to determine their own glucose levels. Unfortunately many such techniques require invasive sampling of the subject.

Impedance spectroscopy practitioners have attempted to determine glucose concentration noninvasively. Stated another way, impedance spectroscopy practitioners have attempted to determine glucose concentration in a body liquid by analyzing the interaction of electromagnetic waves with the target material. The goal of such a technique is to provide a non-invasive in-vivo analysis.

U.S. Pat. No. 5,792,668, incorporated herein by reference in its entirety, describes one example of a device for measuring blood level glucose. According to this patent, one brings two electrodes into direct contact with the human body and attempts to measure the impedance between the electrodes.

However, one drawback of conventional impedance spectroscopy involving the direct contact of two electrodes with the human body is that the results often depend to some extent on variables affecting the electrical contact between the body and the electrodes, such as variables describing the surface condition of the body at the point of contact. As a consequence, such techniques have limited resolution in the measurement of the concentration of blood level glucose. Thus, a need remains for methods and systems for the accurate, effective, and noninvasive determination of the concentration of a substance (such as glucose) in a target (such as a body liquid). Furthermore, a need remains for methods and systems for non-invasively determining the concentration of a substance in a target, the methods and systems being applicable in other contexts such as in environmental monitoring and in food processing.

SUMMARY OF THE INVENTION

The invention relates to systems, methods and devices for accurately and effectively determining the concentration of a substance in a target. Examples of targets include: an in-vitro or an in-vivo target containing body liquid; non-body liquids such as wastewater or beer; and non-liquids such as baby food or biological tissue. One can apply the invention in fields such as biotechnology, medicine, industry (such as corrosion testing), environmental monitoring, agriculture, and manufacturing (such as food manufacturing).

In a first aspect of the invention, the invention provides a device that determines the concentration of a substance in a target. The device includes a first electrode, a signal source, a measuring circuit, and a data processor.

In one embodiment of the device, the first electrode can be electrically insulated from the target, e.g., a cover layer of insulating material covers the first electrode. Hence, the measured parameter(s), e.g., the magnitude of the impedance, does not depend on the surface conditions of the target to the extent it does when two electrodes are in direct contact with a target. Rather, the device capacitively couples a signal to the target and the measured parameter depends therefore primarily on the conditions within the target. The parameter measured in this way can then be converted to the desired concentration, e.g., by using calibration data.

Depending on the frequency, in one embodiment the first electrode is part of a sensor, e.g., a microstrip nearfield antenna or at lower frequencies a fringing capacitor. In one embodiment the microstrip nearfield antenna includes a microstrip electrode, i.e., the first electrode, surrounded by a ground electrode. In this two-electrode embodiment, a modulated voltage is applied between the microstrip electrode and the ground electrode. By using two electrodes, a defined field can be established within the target. One embodiment of a method according to the present invention places the second electrode, i.e., the ground electrode, in electric contact with the target.

The measured parameter preferably depends on the electrical impedance of the sensor. It has been found that the concentration of various substances in the target, for example substances that can change electrical properties of the target (such as colloids suspensions, electrolytes, bio molecular solutions, dyes etc., affects the impedance because it changes the loss (i.e., loss of power) properties and/or the dielectric properties of the target.

In one embodiment, the sensor forms part of a resonant circuit, which is operated at or close to its resonance frequency. Under such conditions, a change of the dielectric properties or loss properties of the target leads to shifts in the parameters of the resonant circuit and can therefore be measured.

The target can be a liquid including body liquids such as blood, extracellular fluid, intracellular fluid, interstitial fluid, and transcellular fluid, measured in vivo or in vitro. The device also can be used to measure tissue flux in a body. Various diseases can impede tissue flux, i.e., microvascular blood flow, reducing supply of necessary molecules leading to alterations in the skin and tissue structure and thus having an impact on the impedance pattern produced by the tissue in question.

Embodiments of the invention also can be used with targets containing non-body liquids such as water in rivers, lakes, puddles, streets, waste-treatment systems, liquids present in foodstuffs, liquids present in growing crops, and liquids used during manufacturing processes.

Embodiments of the invention provides systems for measuring the concentration of a substance in a target, such as the glucose level in blood or tissue. The systems include a sensor having a strip electrode and a ring electrode arranged at the target. In one embodiment, the ring electrode is adapted for direct electrical contact with the target while the strip electrode is electrically insulated therefrom (in an alternative embodiment, the strip electrode can be in electrical contact with the target and the ring electrode be electrically isolated from the target). The strip electrode is adapted to provide a large interaction length with the target. The ring and strip electrodes form a capacitor in a resonant circuit. A modulated voltage in the MHz range close to or at the resonance frequency is applied to the electrodes and the system measures the response of the target. This arrangement permits a high accuracy measurement.

In another aspect, the invention provides a method for determining the concentration of a substance in a target. The method includes arranging a sensor, e.g., a microstrip nearfield antenna (having a microstrip electrode) at the target wherein at least part of the sensor can be electrically insulated from the target. The method includes applying a modulated electrical voltage to the sensor for generating a modulated field in the target. The method further includes measuring at least one parameter (for example the amplitude or the impedance, the phase shift, and/or the frequency), the parameter depending on a response of the target to the field. The method also includes determining the concentration of the substance in the target based at least in part on the measured parameter In one embodiment, the method can include providing a sensor (e.g., a microstrip nearfield antenna with both a microstrip electrode and a second, ground electrode and placing the second, ground electrode in electrical contact with the target), so that, in the antenna example, the modulated electrical voltage is applied between the microstrip and the ground electrodes.

In another embodiment, the method includes measuring the temperature of the target and using the measured temperature in the determination of the concentration. In at least one embodiment, the response of the target is measured by arranging a near field microstrip antenna in proximity to the target.

One can use embodiments of the invention for in-vivo measurements of the human body. Thus, embodiments of a device according to the invention include an elongate electrode having a width much smaller than its length. Embodiments of the invention also include a holder to mount the elongate electrode to an arm or a leg with the longitudinal axis of the electrode extending parallel to the longitudinal axis of the arm or leg. The methods and devices of this aspect of the invention have been found to be especially suited for measuring the glucose concentration in body fluid.

One can also use embodiments of the device according to the invention in other medical and/or biochemical applications. Such applications include: monitoring the concentrations of substances such as glucose or sodium chloride during biochemical processes; detection of changes in tissues of the body, such as those resulting from inflammatory processes in skin and underlying tissues, skin or breast cancer, and edemas; measuring tissue flux; and tracking concentrations of substances in infusions, fermenters, and cell suspensions.

In addition, one can use embodiments of the invention in industrial applications. Industrial applications include: waste water analysis; measuring salt in bodies of water including street water; corrosion testing, and environmental monitoring.

Still other applications of embodiments of a device according to the invention include monitoring the growth and harvesting of agricultural products and food and beverage processing applications. For example, one can use embodiments of the invention in connection with production of brewed and/or fermented beverages, production of baby food, production of dairy products, growing of agricultural products, and production of ingredients used in food and beverage processing, such as high fructose corn syrup.

Still another embodiment of the invention provides a system for measuring the concentration of a substance, e.g., a polluting or toxic substance, in a target, such as in product flow or in wastewater. In one embodiment, the system includes a sensor (e.g., a microstrip nearfield antenna, having a microstrip electrode surrounded by a ground electrode) arranged at the target. In the antenna example, the ground electrode is adapted for direct electrical contact with the target while the microstrip electrode can be electrically insulated there from. The ground and microstrip electrodes form a capacitor in a resonant circuit. The system is adapted to apply a modulated voltage in the appropriate range for the target, e.g., in the MHz range, and close to or at the resonance frequency of the circuit. The system is adapted to apply the appropriate range to the electrodes and the system measures the response of the target.

The system can include or can be adapted to interface with a process control device such that the process being observed is managed at least under certain circumstances (e.g., when a specified concentration of a pollutant is exceeded during the process) based on impedance spectroscopy data.

Details relating to these and other embodiments and aspects of the invention are described more fully in the detailed description and with reference to the accompanying drawings.

BRIEF DESCRIPTION OF THE DRAWING

The invention will be better understood and objects other than those set forth above will become apparent when consideration is given to the following detailed description thereof. Such description makes reference to the annexed drawings, wherein.

The drawings are not necessarily to scale, emphasis instead generally being placed upon illustrating the principles of the invention.

DETAILED DESCRIPTION OF THE INVENTION

Figure 1:
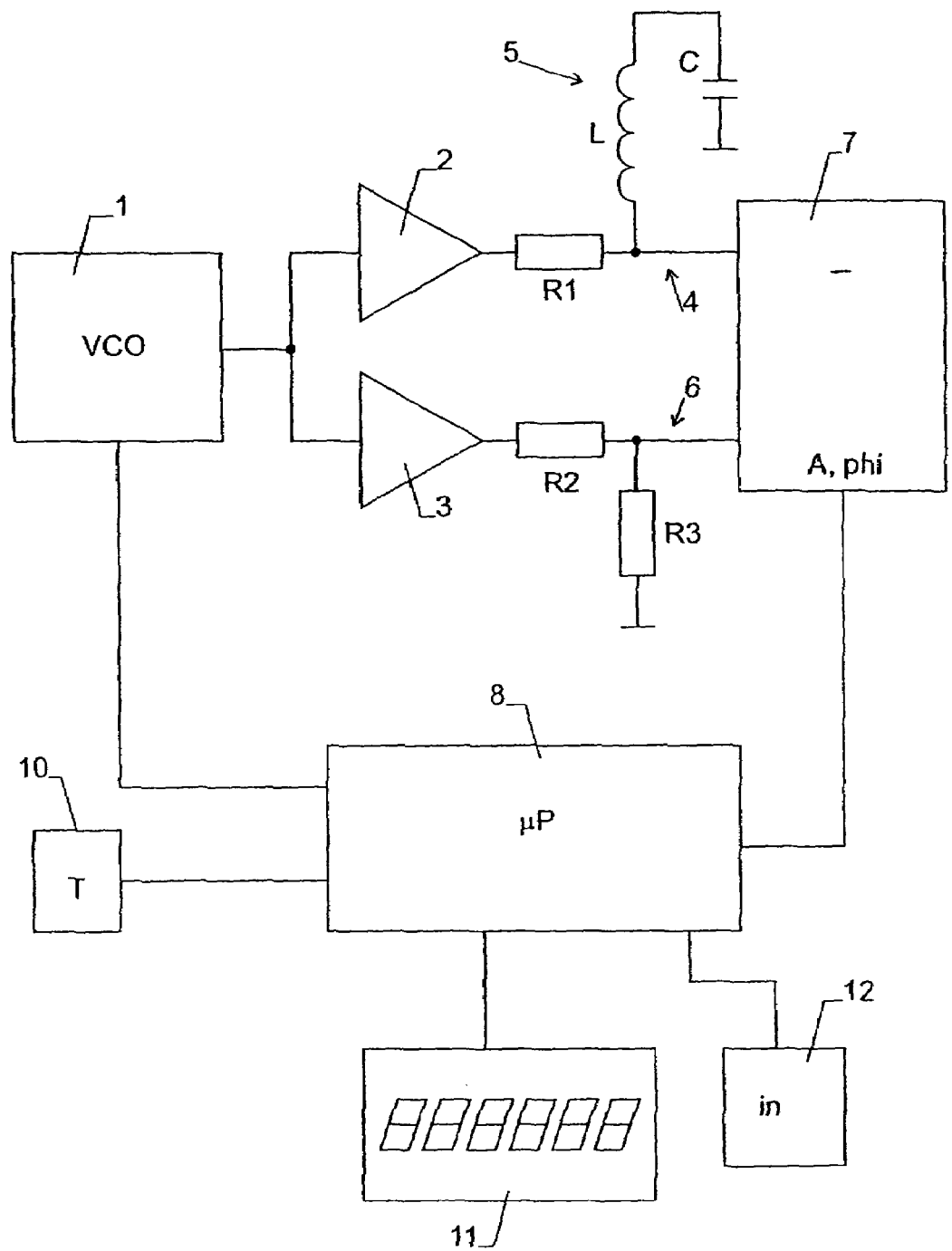
FIG. 1 is a block circuit diagram of a one embodiment for carrying out the invention.

FIG. 1 shows a block circuit diagram of one embodiment of a device according to the invention. The device includes a voltage controlled oscillator (VCO) 1 as a signal source for generating a waveform, e.g., a sine wave signal, the frequency of which depends on an input control voltage. This signal is fed to two amplifiers 2, 3 (In the alternative embodiment of FIG. 11, the signal is fed to a single amplifier 2). The output of first amplifier 2 is connected via a resistor R1 to a first signal path 4. A resonant circuit 5 comprising an inductance L and a capacitor C in series is connected between first signal path 4 and ground. The output of second amplifier 3 is connected via a resistor R2 to a second signal path 6. Second signal path 6 is substantially identical to first signal path 4 but comprises a resistor R3 as a reference load instead of resonant circuit 5.

Both signal paths 4, 6 are fed to a measuring circuit 7, which determines the relative amplitude A of both signals as well as, optionally, their mutual phase shift, phi. Relative amplitude A can be, e.g. the amplitude of first signal path 4 in units of the amplitude of second signal path 6 (wherein the amplitudes are the peak values of the sine waves). In one embodiment, circuit 7 is a conventional circuit for measuring the relative amplitude of both signals.

The output signal of measuring circuit 7 is fed to a microprocessor 8, which also controls the operation of VCO 1.

As can be seen from FIG. 1, the device in the present embodiment further includes a temperature sensor 10, a display 11 and an input device 12 with user operable controls, all of which are coupled to microprocessor 8.

Inductance L of the device of FIG. 1 can be generated by a coil and/or by the leads and electrodes of capacitor C. The inductance values can range depending on various factors including the substance and target of interest. In the case of determining the concentration of glucose in a body liquid, the inductance value ranges between about 220 nH and about 470 nH. One embodiment uses a value of about 330 nH.

Figure 6:
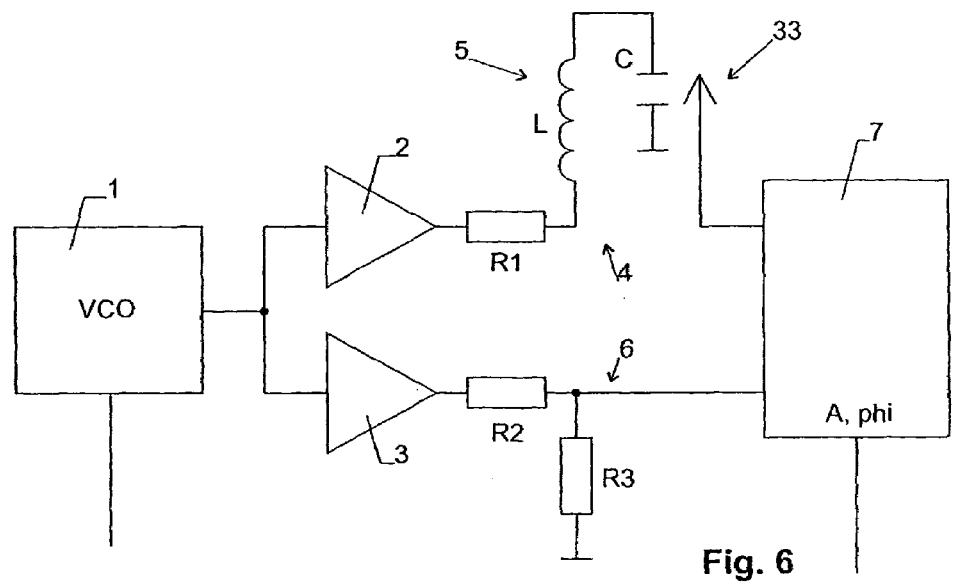
FIG. 6 is a second embodiment of the circuit.
Figure 7:
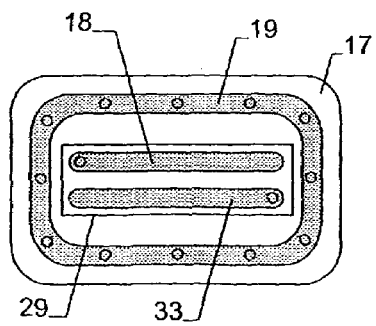
FIG. 7 is an alternative electrode geometry, FIG. 8 a third embodiment of the circuit.

A sensor (e.g., a near field microstrip antenna, making up part of the capacitor C of the device of FIG. 1) probes a target. In other words, the device of FIG. 1 includes a capacitor C having electrodes adapted for placement near the target. In one embodiment, the near field microstrip antenna is located close to the target but remote from the rest of the device of FIG. 1. This arrangement can be useful in situations where the target itself may present an environment that could be damaging to all or part of the device (e.g., applications where the target comprises running water, such as waste water monitoring and/or environmental monitoring). With reference to FIGS. 6 and 7, in one embodiment, the device of FIG. 1 includes an extra antenna electrode 33 that is in electrical communication with the device but is located remote from the device.

The geometry of the electrodes is such that the electric field generated by them extends into the target. Representative examples of suitable geometries are discussed below. As mentioned above, at least one of the electrodes of the capacitor is electrically insulated from the target such that capacitor C is primarily a capacitive load, the capacitance and loss of which depends on the electrical properties (i.e. the response) of the target at the frequency of VCO 1.

The depth of the electromagnetic fields produced is strongly dependent on the electrode/antenna geometry (defined by the distance of the microstrip and the ground electrodes as well as by the shape of the microstrip antenna/electrode itself). Decreasing the distance between the microstrip electrode and the ground electrode increases the density of the electromagnetic field lines produced by the electrodes. The shape of the microstrip antenna itself has an impact as well. More generally, the configuration (e.g., frequency used) and dimensions of a sensor for use with the invention depend on the application (e.g., water content and dimensions of the object).

To measure the concentration of a substance in the fluid of the target, one embodiment of microprocessor 8 can initiate a measurement cycle consisting of a frequency sweep of VCO 1. The sweep can start at a frequency fmin below the expected resonance frequency f0 of the resonant circuit 5 and extend to a frequency fmax above resonance frequency f0. The sweep from fmin to fmax can occur as a single sweep or as a sequence of discrete sweeps. Each sweep provides a set of data points useful in calculating the concentration of the substance in the liquid. In one embodiment, the VCO is a symmetrical VCO to provide low harmonics and is a FET implementation providing a relatively wide frequency range. A symmetrical VCO cancels out most of the first harmonic because a differential signal is used. A FET implementation provides a higher frequency range as less parasitic capacitance exists in the resonating circuit because the FET Gate can be controlled directly avoiding a capacitive coupled feedback.

Figure 5:
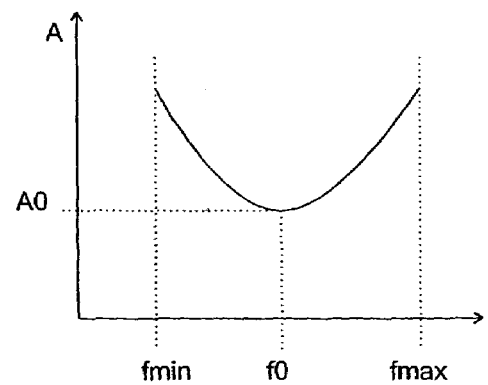
FIG. 5 shows the behavior of the relative amplitude A as a function of frequency.

Note also that the range of the frequency sweep may be influenced by the application and/or the equipment used. For example, sweeps performed on a living body may use a lower fmax than sweeps performed on a target other than a living body. During the sweep or series of sweeps, the electrical properties of signal path 4 will change substantially, while those of signal path 6 will vary only slightly. The amplitude determined by measuring circuit A will therefore fall to a minimum A0 at f0, as shown in FIG. 5. At the same time, phase shift phi crosses zero.

FIRST EXAMPLE APPLICATION

Measurement, e.g., In Vivo Measurement, of a Substance, e.g., Glucose, in a Body Liquid, e.g., Blood The specific conductivity $\rho(f)$ and the dielectric constant $\epsilon(f)$ for a given fluid vary depending on the type of fluid. For example, it is presently believed that the specific impedance of at least some body fluids (i.e. the specific conductivity $\rho(f)$ and the di-electric constant $\epsilon(f)$) in a frequency range between 10 MHz and 2000 MHz, more particularly between 20 MHz and 70 MHz and most particularly between 38 MHz and 58 MHz, is a function of the properties and concentration of the salty (ionic) components of the human body, related to variations in blood glucose. These salty components primarily include solvated sodium, potassium, calcium and other minor ions and their counter ions, the primary counter ion being chloride.

In one embodiment of the invention, only amplitude A0 is measured as a parameter for the determination of the concentration of the substance. Suitable calibration data stored in microprocessor 8 is used to convert amplitude A0 into the desired concentration level. In this example, the calibration data stored in microprocessor 8 is calibration data that is appropriate for the measurement of glucose in blood. In one embodiment, the calibration data includes an offset $\alpha 0$, a factor $\alpha 1$ for the relative amplitude and a factor $\alpha 2$ for the temperature correction. Thus, the resulting concentration equals $\alpha 0 + \alpha 1 *$(measured impedance)$+ \alpha 2 *$temperature. Measurements of other types of targets, as described herein, may have their own respective types of calibration data.

In the example of measuring glucose levels in blood, the effects exploited for the measurement are temperature dependent. Temperature has an effect on permittivity and conductivity. Temperature appears to have a nonlinear effect on the measurement of impedance conducted in vivo with the current glucose monitoring device, that originates from nonlinear physiologic responses of the human body to temperatures conditions and changes. Changes in temperature have a more or less linear effect on ac conductivity per se. However, the human body reacts physiologically in a nonlinear way to changes in temperature. Thus, other embodiments of the invention take into account an appropriate temperature correction in applications where the target shows temperature dependence, e.g., nonlinear temperature dependence.

In order to obtain high accuracy over a wide temperature range, one brings temperature sensor 10 into thermal contact with the target. In the present example, the temperature sensor 10 does not need to be in physical contact with the target (i.e., blood or other liquid) being measured. Rather, the temperature sensor 10 can contact the skin to obtain temperature. The signals from temperature sensor 10 are used to correct the obtained result, again using calibration data obtained from calibration measurements.

Figure 2:
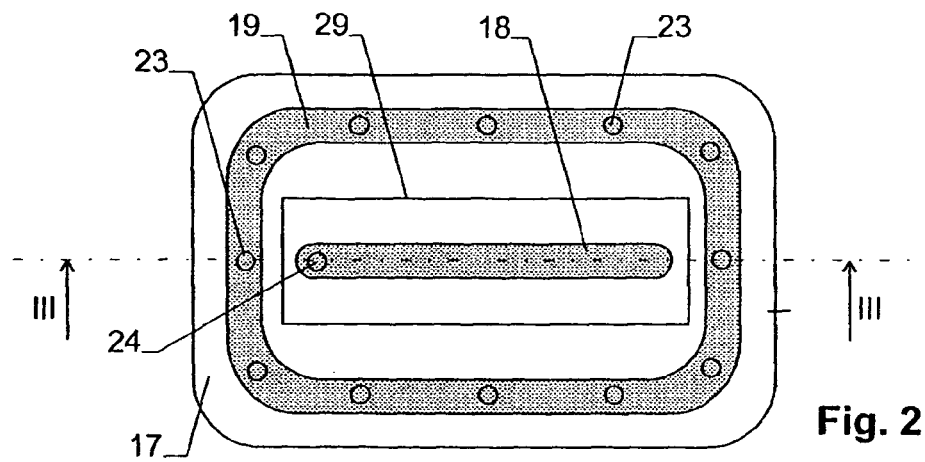
FIG. 2 is a view onto a possible embodiment of the device.
Figure 3:
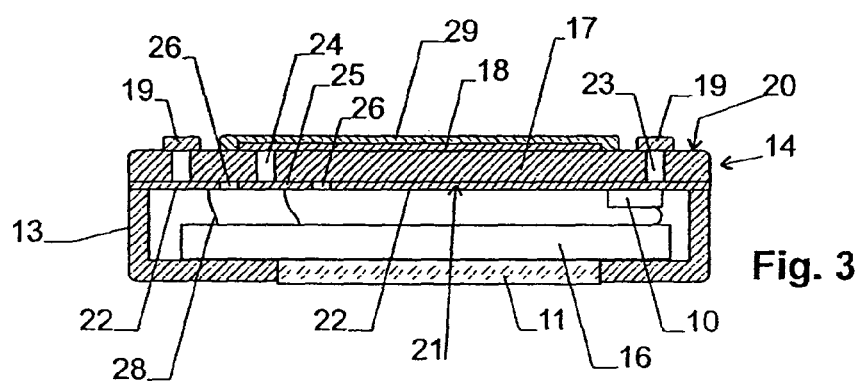
FIG. 3 is a section along line III-III of FIG. 2.

A proper design of the electrodes of capacitor C permits optimization of the accuracy and sensitivity of the present device in a given application. Example geometry of a device suitable for taking in-vivo measurements in a living body is shown in FIGS. 2 and 3.

The device comprises a housing 13 closed on one side by an electrode plate 14. The display 11 is arranged opposite electrode plate 14. The electronic circuits 16 are arranged between electrode plate 14 and display 11.

Electrode plate 14 can include an electrically insulating substrate 17 with a sensor, e.g., a microstrip nearfield antenna having a microstrip electrode 18 and a top or ring/ground electrode 19 arranged on an outer side 20 thereof. A bottom electrode 22 covers an inner side 21 of insulating substrate 17. A plurality of through-contacts 23 is provided to connect ring/ground electrode 19 to bottom electrode 22. A further through-contact 24 connects one end of microstrip electrode 18 to a small bond pad 25 arranged in an opening 26 of bottom electrode 22 on inner side 21.

Temperature sensor 10 is mounted to bottom electrode 22. The large number of through-contacts 23 ensure that bottom electrode 22 follows the temperature of ring/ground electrode 18 and therefore the temperature of the target closely.

A typical size of electrode plate 14 is 32 mm ×21 mm. Bottom electrode 22 covers all of inner side 21 except for the small opening 26 and is therefore much larger than strip electrode 18.

Leads 28 are provided to connect bottom electrode 22, contact pad 26 and temperature sensor 10 to the electronic circuits 16.

While bottom electrode 22 and ring/ground electrode 19 are connected to ground, strip electrode 18 is connected to inductance L of resonant circuit 5. Therefore, the capacitor C is formed between strip electrode 18 as a first electrode and ring electrode 19 and bottom electrode 22 as a second electrode. In other words, the second electrode consists of two electrode layers: a top electrode layer formed by ring electrode 19 and a bottom electrode layer formed by bottom electrode 22.

An electrically insulating cover layer 29 covers all of strip electrode 18 but not ring electrode 19. In other words, strip electrode 18 is arranged between substrate 17 and cover layer 29. Cover layer 29 is preferably made of a hard, moisture- and salt-impervious material such as glass, ceramics, a polycarbonate or diamond-like carbon (DLC) of a thickness preferably between 50 and 100 μm.

FIGS. 2 and 3 illustrate a device that may be especially useful in applications where the device is to be disposed against a substantially flat surface, such as an area of skin on a living body. The geometry and orientation shown in FIGS. 2 and 3 are not limiting, however. Many different orientations, shapes, and sizes are usable in accordance with the invention. For example, the display 11 may be disposed along a side of the housing 13, or may be entirely separate from the housing 13 (e.g., in operable communication with the electronic circuits 16 but disposed at a location remote from the housing.)

In another embodiment, the display 11 and electronic circuits 16 are disposed within a first housing while the electrode plate 14 (or other configuration of electrodes) is disposed within a second housing, the electrodes being in operable communication with the electronic circuits 16. This configuration may be advantageous in embodiments of the invention that are used for applications and/or in environments that could cause damage and/or stress to the electronic circuits 16 and/or the display 11.

Figure 4:
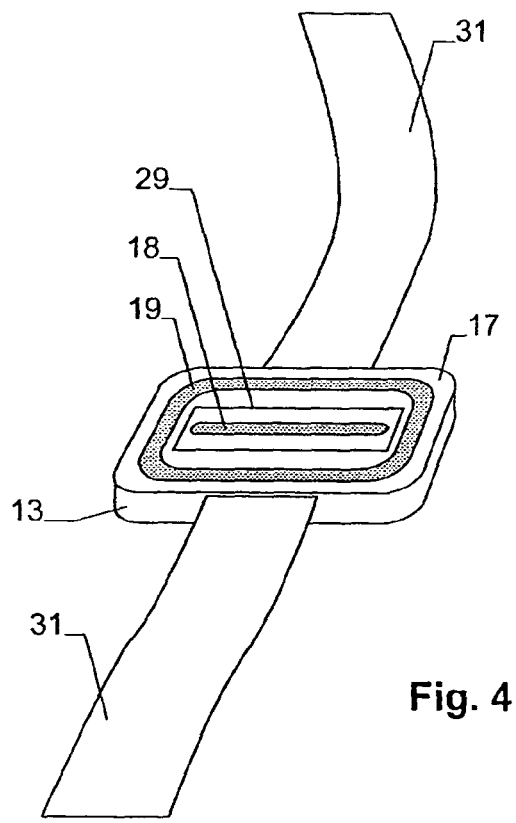
FIG. 4 is the device of FIG. 3 with a wristband.

As can be seen in FIG. 4, a holder or wristband 31 is attached to housing 13 for fixing the device to an arm or a leg of a human body with cover layer 29 facing the body and a longitudinal axis of strip electrode 18 parallel to the arm or leg. In this way, ring electrode 19 comes into contact with the user's skin and the ring electrode and the area of the user's body in contact with the ring electrode come to a common reference potential.

As described above, a pure sine voltage has been found to be sufficient for the measurements. However, other types of modulated voltages, such as square-wave voltages or pulses can be used as well. In this case, measuring circuit 7 is preferably provided with suitable filters for selectively sampling one or more frequency components. At least one measured frequency component is preferably close to the resonance frequency of resonant circuit 5 for exploiting the circuit's high sensitivity to the target's properties at that frequency.

The electrode geometry can be varied for adapting it to a given application. While the design of FIG. 2 is optimized for a measurement on an arm or leg, a circular design can be used for measurement on a flatter body part or an in-vitro sample. Further, in embodiments of the invention that are used in the manufacturing, environmental, and/or agricultural industries, the electrode may have a geometry adapted for the given application, such as a partially-curved shape, a ring-like shape, a triangular shape, and a cylindrical shape. These other applications are described further herein.

Ring electrode 19 does not necessarily have to form a closed ring as long as it provides sufficient grounding of the site (e.g., in this example, the body part) to be measured. The ring electrode 19 can, e.g., also have a U-shape or consist of two stripes parallel to and laterally enclosing strip electrode 18. Ring electrode 19 can also be omitted completely or be covered by cover layer 29, especially for measurements (such as in-vitro measurements) where noise is low.

Part of one embodiment of an alternative embodiment of a circuit according to the invention is shown in FIG. 6. In FIG. 6, there is no direct wired connection between resonant circuit 5 and measuring circuit 7. Rather, an antenna electrode 33 is located in proximity to the electrodes of capacitor C, and measuring circuit 7 measures the signal returned by antenna electrode 33.

A possible arrangement of the electrodes for the circuit of FIG. 6 is shown in FIG. 7. As can be seen, antenna electrode 33 is strip shaped and arranged in parallel to strip electrode 18. Both, antenna electrode 33 and strip electrode 18 are covered by cover layer 29 and therefore electrically insulated from the target.

The device of FIGS. 6 and 7 is again sweeping VCO 1 between a frequency fmin below the resonance frequency f0 of resonant circuit 5 and a frequency fmax above it. In contrast to FIG. 5, measuring circuit 7 now detects a maximum amplitude A0 at f0, wherein the value of A0 depends on the response, i.e. the electrical properties of the target at the resonance frequency f0. Changing the resonant circuit to a tank circuit also changes the resonance curve in a way that a maximum rather then minimum amplitude results. The parameter A0 can now again be processed using calibration data as described above.

Figure 8:
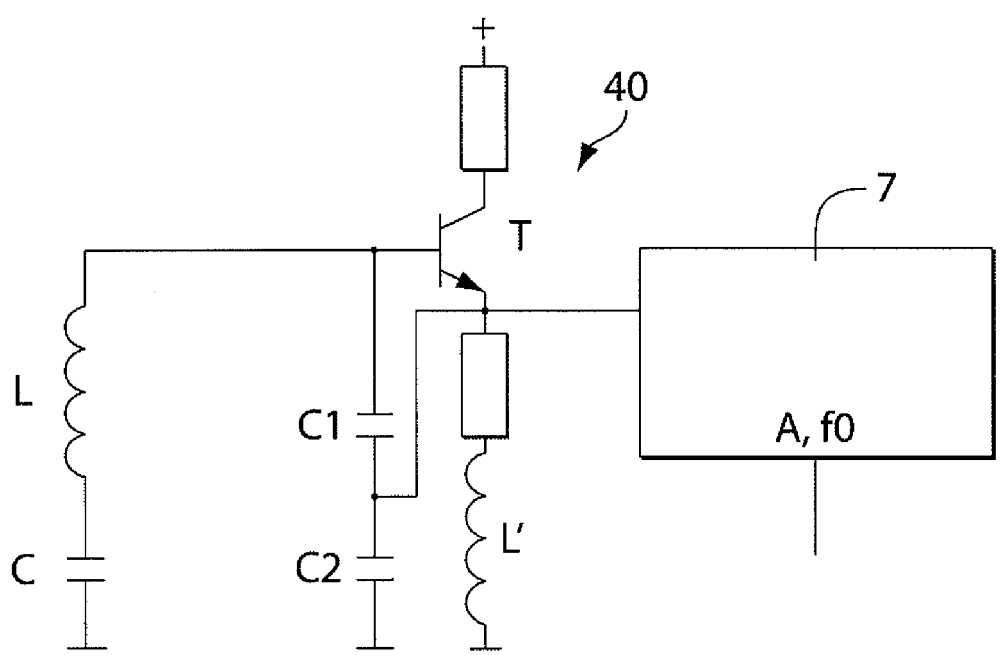

A second embodiment of a circuit is shown in FIG. 8. Here, the capacitor C formed by the electrodes is part of the resonant tank circuit of an active, self-oscillating oscillator 40. The amplitude A and frequency f0 of the output signal of oscillator 40 depend on the capacitance and losses in capacitor C. The corresponding signal is fed to measuring circuit 7, which evaluates the parameters A and f0. Measuring the corresponding parameters A and f0 again allows a sensitive measurement of the desired concentration using calibration data.

In the examples shown so far, the invention was used in a device for qualitatively or quantitatively displaying the concentration a substance (such as glucose) in body liquid. The invention can, however, also be used in devices that automatically administer medication to a body, such as an insulin pump, where the amount and/or time for administering the medication depends on the measured concentration of the substance in question. The invention can also be used in any other type of device that requires the measurement of the concentration of a substance in a target.

SECOND EXAMPLE APPLICATION

Monitoring Concentrations of Substances During Biochemical Processes

Another aspect of the invention is directed to using the above-described device in other medical and/or biochemical applications, such as monitoring the concentrations of substances that can change electrical properties of the target such as sodium during biochemical processes. Biochemical processing is essential to many food, chemical, and pharmaceutical industries. At least one embodiment of the invention is directed to an application of the above-described device that is suitable for serving as a measuring device for defined levels of a substance in a liquid during a biochemical process in a bioreactor.

One example of a biochemical process for which the invention may be used is in connection with a fermenter. Fermentation is one typical biochemical process that may be used in the production of products such as organic acids or dairy products. The fermenter is an important part of an ethanol production process. Ethanol may be produced in a fermenter during the biodegradation of glucose by yeast. After sterilizing, the glucose solution is fed to a fermenter. Nutrients to support cell growth may also be provided.

The production of a chemical such as ethanol may be monitored to improve the efficiency of the process. One way this can be accomplished using the present invention is by providing a fermenter with an online sensor or a plurality of online sensors constructed and arranged to track a concentration of product(s) during the fermenting process. Impedance spectroscopy techniques according to embodiments of the invention can use data provided by these sensors to provide a non-invasive and online way to monitor alcohol production.

Figure 9:
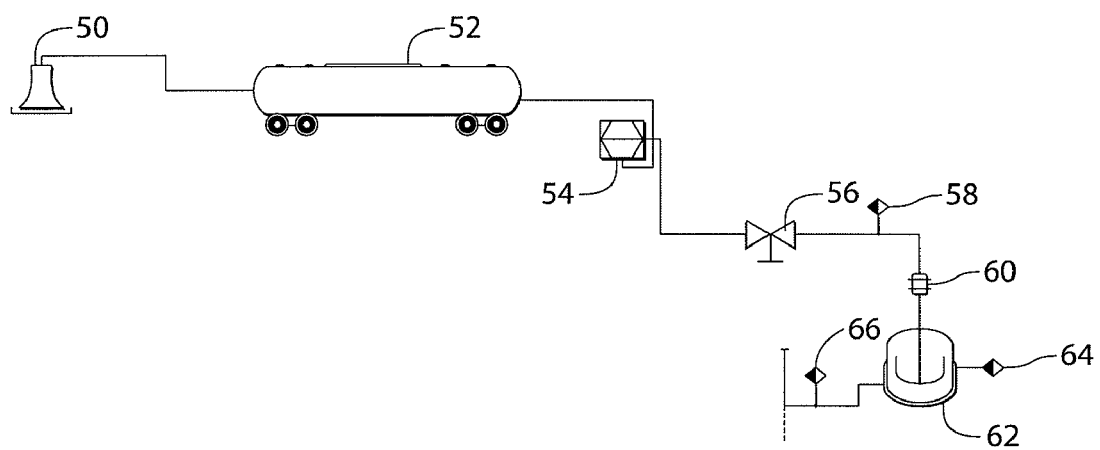
FIG. 9 is a schematic of a system using the circuit of FIG. 1, in accordance with an embodiment of the invention.

More generally, with reference to FIG. 9, an initial process 50 can produce product that is then transported 52 to a new location. The product is then pumped into fermenter 54. A valve 56 controls flow of the product. A sensor 58 monitors the concentration of a substance of interest in the product. Elements 60 and 62 perform a second process on the product. Sensor 64 monitors the concentration of a substance of interest during the second process and sensor 66 monitors the concentration of a substance of interest in the waste flow from the second process. In one embodiment, one or more of the sensors can provide data to a control on the valve to allow the control to manage the valve based at least in part on the sensor data. For example, if the concentration of a substance of interest goes too high, the valve control may shut the valve.

In addition, the devices and methods as applied to the monitoring of fermentation may also be applicable to monitoring the manufacture and processing of brewed and/or fermented beverages, such as beer, in a substantially similar manner to that described above.

Figure 10A:
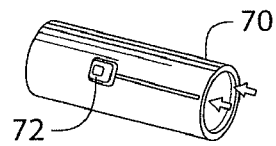
FIGS. 10A-F illustrate alternative embodiments of systems or portions of systems for monitoring processes such as the process illustrated in FIG. 9.
Figure 10B:
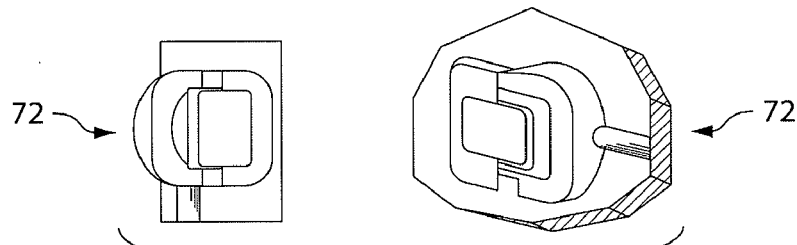
Figure 10C:
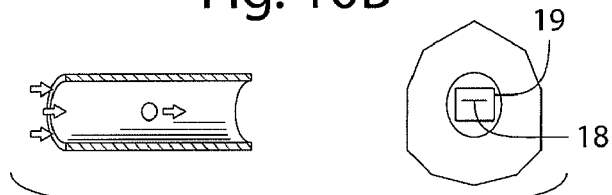
Figure 10D:
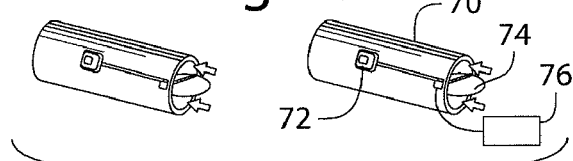
Figure 10E:
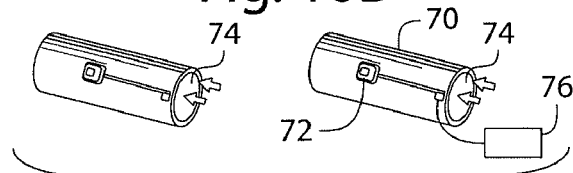

FIGS. 10A-F show various configurations of systems for monitoring processes as described above. With reference to FIG. 10A, a pipe 70 is transporting product, e.g., wastewater, and a sensor 72 is mounted to the pipe 70. With reference to FIG. 10B, the sensor 72 is shown in greater detail mounted onto/into a pipe. In one embodiment, the configuration of the sensor 72 is a shown in FIGS. 2 and 3. With reference to FIG. 10C, an interior section of the pipe shows the microstrip 18 and the ring electrode 19, the ground is actually in touch with the target, i.e., the product. Yet the microstrip can be electrically insulated from the target. FIGS. 10D and E show the same configuration with the sensor providing data to a valve control 76 associated with a valve 74 in the pipe 70. Thus, the sensor 72 provides data, e.g., concentration measurements of a substance of interest, to a control element 76, e.g., a valve controller other process controller. In the valve control embodiment, the valve control manages, e.g., closes, the valve based at least in part on the sensor data.

Figure 10F:
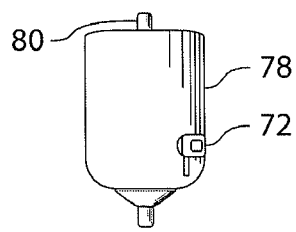

Finally, with reference to FIG. 10F, a fermentor 78 having an input pipe 80 can have a sensor 72 mounted on it. The sensor can monitor the progress of a reaction. The fermenter can brew a product where electrolyte concentration is changing, or the fermenter can brew beer where the concentration of a substance of interest is monitored.

THIRD EXAMPLE APPLICATION

Detecting changes in Body Tissue

Inflammatory processes in the body have a characteristic impact on the impedance pattern of living tissue (in both humans and animals). Thus, in at least one embodiment, the devices and methods of the invention may be applied to diagnose changes in tissue, such as those resulting from inflammatory processes in the body, cancer, and edemas.

Edemas are accumulations of water in tissues (although water in cells and serous cavities also may be considered to be edemas as well). These accumulations of water show a significantly different impedance pattern compared to that of healthy tissue. Using devices and methods such as described herein, at least superficial edemas could be discriminated from normal tissue, in a non-invasive, quick, inexpensive, and relatively pain-free manner.

Thus, one can use an embodiment of a device according to the invention to detect edemas by sizing the housing and the electrodes to fit over the area of the body being measured.

Furthermore, certain electrical properties of tumor cells differ from those of the normal tissues that surround them. Tumor cells demonstrate greater permittivity (ability to resist the formation of an electrical field) and conductivity of electrical current. These findings are thought to occur because (a) cancer cells tend to have higher sodium and water content than normal cells, and (b) their cell membranes have different electrochemical properties. Thus, the devices and methods of the invention could be applied to detect other types of changes in the tissue of a body, especially changes detectable near the surface of the skin, such as skin cancer, breast cancer, and some types of tumors.

FOURTH EXAMPLE APPLICATION

Determining Conditions of Cells During Processing

During various types of processes (such as biochemical processes, and growth of cell cultures), batches of cells sometimes produce low yields because of partly damaged cells, e.g., damaged cell walls or membranes. It can be difficult to evaluate the presence or extent of this type of damage prior to the start of a process. However, impedance spectroscopy techniques, such as those techniques used in the devices and methods of the invention, may be used to assess the quality of a given cell before a process moves to the next production step.

It is believed that a cell and its surrounding environment can act like a simple circuit having characteristic impedance. The cell cytoplasm and the extracellular space (which has a conductivity) comprise resistive components of the impedance. The cell membrane itself contributes capacitive effects to the impedance, especially as the frequency to which the cell is subjected is increased. By characterizing "high quality cells" at a given frequency range, it is possible to use the systems and methods of the invention to monitor cells to determine their condition relative to the. "high quality cells". For example, changes in impedance may reflect deviations from normal in the cell membrane. This may also be done with cells in suspension.

FIFTH EXAMPLE APPLICATION

Monitoring Concentrations of Substances in Infusions

At least one aspect of the invention is directed to an application of the above-described device that is suitable for tracking concentrations of substances in infusions. For example, the devices and methods of the invention can be applied for monitoring solutions in medical use, such as sodium, potassium, or other salt solutions, to ensure constant flux and concentration. A standard Sodium Chloride infusion given to a patient basically involves three risks:
a) is it really NaCl and not KCl
b) is it the correct concentration
c) is it still running (drift of the rate of infusion)

The above issues are particularly interesting for prenatal care units. Thus, embodiments of the present invention can be utilized to verify concentrations and operation at the point of delivery.

SIXTH EXAMPLE APPLICATION

Monitoring the Production of Foodstuffs

Use of the invention in the growth and/or production of food and/or beverages can help to ensure the quality and safety of the resulting products and can also save time in the growth and/or production process. Examples of use of embodiments of the invention in such processes are shown in FIGS. 9-10F.

For example, at least one aspect of the invention is directed to an application of the above-described device that is suitable for testing foods and beverages, both during growth and during processing. In this aspect, the invention is used to monitor the concentration of a substance (e.g., water and sodium chloride) in a food and/or beverage product being produced, such as baby food, dairy products, beer, or wine. During growth or preparation of the food product, the pair of electrodes of the device could be disposed on the surface of the food product, to detect the concentration of a given substance (e.g., sodium) in the food product.

In one embodiment, the devices and methods of the invention are applied to monitor wine processing. The quality of wine is said to depend on a few parameters, one of which is the electrolyte balance and alcohol content. As with the fermentation process described previously, the invention is used to monitor the transformation of glucose into alcohol, so that the process can be stopped when glucose concentration reaches a predetermined level.

In another example, at least one aspect of the invention is directed to an application of the above-described device that is suitable for monitoring water concentration in food and/or beverage products. Monitoring water concentration may be especially useful in improving the timing and efficiency of dairy processes such as the making of butter or cheese, where the water content may have significant impact on the quality of the resulting product.

In another example, at least one aspect of the invention is directed to an application of the above-described device that is suitable for measuring the concentration of water and/or electrolytes in an agricultural product.

SEVENTH EXAMPLE APPLICATION

Wastewater Analysis

Because the devices and methods of the invention can be used to detect changes in water composition, in at least one embodiment the devices and methods of the invention have use in applications such as analysis of wastewater. For example, an accident or error occurring during production at a chemical plant could result in harmful compounds contaminating drainage water exiting the chemical plant. The devices and methods of the invention provide an inexpensive, sensitive method to monitor the exiting wastewater for this kind of occurrence. The device according to the invention may be coupled to trigger an alarm when certain predetermined changes in water composition occur.

Figure 11:
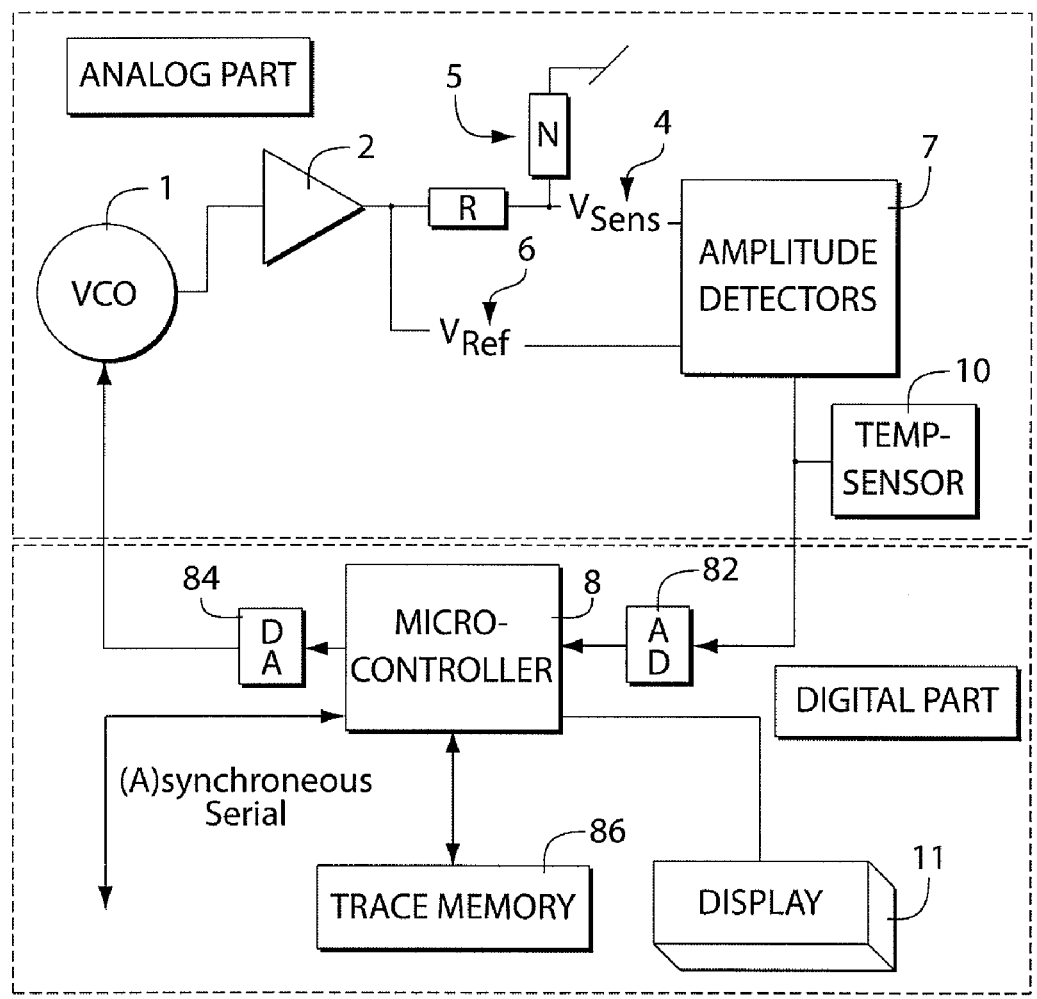
FIG. 11 is a block circuit diagram of an alternative embodiment to the embodiment of FIG. 1 for carrying out the invention.

Further, the devices and methods of the invention may be used throughout the chemical process (e.g., monitoring the status and progress of chemical processes, as described previously for the "biochemical processes" application). Examples of use of embodiments of the invention in such processes are shown in FIGS. 10-11F.

EIGHTH EXAMPLE APPLICATION

Corrosion Testing

The methods and devices of the invention, which use RF impedance spectroscopy, are usable to characterize and measure corrosion. One example of a technique for characterizing corrosion is described in U.S. Pat. No. 4,238,298, incorporated herein by reference in its entirety. Passing an alternating current (A.C.) at a high frequency between two electrodes disposed in a corrosion medium will give the ohmic resistance of the corrosion medium. Passing an AC current at a low frequency between the electrodes gives an impedance that is equal to the sum of the ohmic resistance and the corrosion reaction resistance. The corrosion reaction resistance is inversely proportional to the corrosion rate of the metal in the medium.

The devices and methods of the invention can be adapted to measure the ohmic impedance and the corrosion reaction impedances, as described above, at both low and high frequencies. It is then possible to compute the reciprocal of the difference between the ohmic impedance and the corrosion reaction impedance, to give the corrosion rate.

NINTH EXAMPLE APPLICATION

Measuring Salt in Street Water

Because the methods and devices of the present invention detect the concentration of solutes such as salts in an aqueous solution, one application of the invention is for determining whether a surface (such as a street) coated with water has been treated with a substance such as road salt.

For example, the invention can be used in an automobile, to detect whether a road or street has been salted (such as when it snows). The invention is used in connection with a sensor head located to measure the salt content of the water splashing up from the wheels.

TENTH EXAMPLE APPLICATION

Environmental Monitoring

Waters around industries and ecologically sensitive areas needs to be closely monitored to ensure purity and water quality. The devices and methods of the invention provide a simple, inexpensive way to monitor the quality of the water by monitoring the concentration of water and/or concentration of one or more substances in the water.

While there are shown and described presently preferred embodiments of the invention, it is to be distinctly understood that the invention is not limited thereto but may be otherwise variously embodied and practiced within the scope this disclosure.

What is claimed is:

1. A method for managing a process involving a specimen, the method comprising:
    arranging a first electrode at the specimen, wherein the first electrode is electrically insulated from the specimen;
    receiving a modulated electrical voltage signal at the first electrode to generate a modulated field in the specimen;
    measuring at least one parameter depending on a response of the specimen to the field;
    determining a concentration of a substance in the specimen based at least in part on the measured parameter; and
    controlling an aspect of the process based at least in part on the determined concentration.

2. The method of claim 1 wherein controlling an aspect of the process comprises controlling a valve based at least in part on the determined concentration.

3. The method of claim 1 wherein the method further comprises arranging a second electrode at the specimen and wherein the modulated electrical voltage generates a modulated field between the first and the second electrode.

4. The method of claim 3 wherein the second electrode is in electric contact with the specimen.

5. The method of claim 3 wherein the method further comprises measuring a temperature of the specimen and using the temperature in the determination of the concentration.

6. The method of claim 1 wherein the modulated electrical voltage signal is a sine wave.

7. The method of claim 6 wherein the modulated electrical voltage signal has a frequency between 10 MHz and 2 GHz.

8. The method of claim 1 wherein the method further comprises arranging an antenna electrode at the specimen in proximity to the first electrode and wherein the response of the specimen is measured by measuring a signal transmitted from the first electrode to the antenna electrode.

9. The method of claim 1 wherein the substance is glucose.

10. The method of claim 1 wherein the specimen is a living body.

11. The method of claim 1 wherein the determining the concentration comprises using calibration data to convert the parameter to the concentration.

12. The method of claim 1 wherein the first electrode forms part of a resonant circuit having a resonance frequency and wherein the resonant circuit is operated substantially at the resonance frequency.

13. The method of claim 12 wherein the resonant circuit is at least part of a tank circuit of an active oscillator and wherein the parameter is one of an amplitude and a frequency of a signal generated by the oscillator.

14. The method of claim 1 wherein receiving a modulated voltage comprises receiving a frequency sweeped modulated voltage wherein the frequency is swept from a frequency below the resonance frequency to a frequency above the resonance frequency.

15. The method of claim 1 wherein the substance is an alcohol.

16. The method of claim 1 wherein the specimen is a salt solution.

17. The method of claim 1 wherein the substance is a salt.

* * * * *